United States Patent [19] [11] 4,055,586
Feichtinger et al. [45] Oct. 25, 1977

[54] PROCESS FOR THE MANUFACTURE OF BIS-(2-CYANOETHYL)-AMINE

[75] Inventors: Hans Feichtinger, Dinslaken; Wolfgang Payer, Wesel; Boy Cornils, Dinslaken; Jürgen Weber, Oberhausen, all of Germany

[73] Assignee: Ruhrchemie Aktiengesellschaft, Oberhausen, Germany

[21] Appl. No.: 733,999

[22] Filed: Oct. 20, 1976

[30] Foreign Application Priority Data

Oct. 27, 1975  Germany .............................. 2547977

[51] Int. Cl.$^2$ .................. C07C 120/00; C07C 121/43
[52] U.S. Cl. ............................................. 260/465.5 R
[58] Field of Search ................................ 260/465.5 R

[56] References Cited

U.S. PATENT DOCUMENTS

| 1,992,615 | 2/1935 | Hoffmann et al. | 260/465.5 R |
| 2,401,429 | 6/1946 | Kung | 260/465.5 R |
| 2,579,580 | 12/1951 | Howk et al. | 260/465.5 R X |
| 3,914,280 | 10/1975 | Yamakami et al. | 260/465.5 R |

FOREIGN PATENT DOCUMENTS

| 1,328,088 | 4/1963 | France |
| 1,593,763 | 8/1970 | Germany |
| 2,004,405 | 8/1971 | Germany |

OTHER PUBLICATIONS

Buc, et al.; J.A.C.S., 67(1945), pp. 92–94.
Wiedeman, et al.; J.A.C.S., 67(1945), pp. 1994–1996.

Primary Examiner—Joseph Paul Brust
Attorney, Agent, or Firm—Bierman & Bierman

[57] ABSTRACT

A process for the manufacture of bis-(2-cyanoethyl)-amine wherein gaseous ammonia is reacted with acrylonitrile having a 5–15% by weight water content in a bubble column reactor. The reaction is carried out at a temperature of about 20°–80° C.

5 Claims, No Drawings

PROCESS FOR THE MANUFACTURE OF BIS-(2-CYANOETHYL)-AMINE

This application claims the priority of German application P 2547977.0 filed Oct. 27, 1975.

Bis-(2-cyanoethyl)-amine is a valuable starting material for a number of important syntheses. For example, it can be converted by hydrogenation into dipropylenetriamine which is employed as a hardener for epoxide resins. The great distance between the nitrogen atoms of dipropylenetriamine make it useful in the manufacturing of flexible terminal condensates, in contrast to diethylenediamine which is also used as a hardener. Moreover, the saponification product (iminodipropiolic acid) is useful in the manufacture of polycondensation products.

In order to prepare bis-(2-cyanoethyl)-amine, ammonia is added to acrylonitrile according to the following formula:

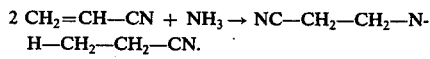

In accordance with a known process, a 28–30th % aqueous ammonia solution is added dropwise to acrylonitrile at 20°– 30° C. The solution is then permitted to react. Even with a residence time of 24 hours, yields of only 85% bis-(2-cyanoethyl)-amine are obtained. [L.R. Buc at al, J. Am. Chem. Soc., 67, 92 (1945).] When the above-mentioned procedure is reversed and the acrylonitrile is added to a 28% aqueous ammonia solution at the same temperature, approximately the same yields are obtained. [O.F. Wiedeman et al, J.A. Chem. Soc, 67, 1994 (1945).] As a result of the long residence times required in the manufacture of bis-(2-cyanoethyl)-amine by prior art methods, large reaction volumes are needed. Thus, under present production methods, large amounts of time and extensive manufacturing facilities are necessary to prepare bis-(2-cyanoethyl)-amine on an industrial scale.

In order to overcome the hereinbefore mentioned drawbacks, the addition of aqueous ammonia to acrylonitrile has been proposed. The reaction takes place under pressure and at temperatures between 50° and 150° C. However, carrying out the reaction under these conditions does not result in an increase in the reaction velocity or in the yield. In fact, instead of forming bis-(2-cyanoethyl)-amine, β-aminopropiononitrile was formed. Further, it was discovered that when liquid ammonia was reacted with acrylonitrile under pressure at 90° C., the end product consisted of 80% bis-(2-cyanoethyl)-amine and 20% β-alanine nitrile [O. Bayer, "Angewandte Chemie", 61, 234, (1949).]

It is the object of this invention to develop a process which allows the selective addition of one mole of ammonia to two moles of acrylonitrile at a high reaction velocity and under normal pressure with the formation of bis-(2-cyanoethyl)-amine in high yields. Using the method of the present invention, it was found surprisingly that bis-(2-cyanoethyl)-amine can be successfully manufactured by reacting gaseous ammonia with acrylonitrile which contains 5 to 15% water by weight in a bubble column reactor. Thus, by using the method of the present invention, it is now possible to shorten the residence times previously required to obtain high yields.

The bubble column which is used as the reactor in accordance with the method of the present invention is well known to experts in this field. There is, for example, a description of this type of reactor in Ullmann's Encyclopadie der technischen Chemie, Vol. 3, page 369, (1973). The bubble column reactors used in the present invention preferably have a ratio of the diameter to the length of about 1 : 5 to 1 : 20.

The water in the acrylonitrile must be maintained at a concentration of about 5 to 15% by weight in order to insure that bis-(2-cyanoethyl)-amine is formed. The reaction can be continuous or batch type and the starting materials are fed into the reactor in a counter-current fashion. The reaction should be carried out at a temperature range of 20° to 80° C.

It is advantageous to introduce the acrylonitrile into the reactor at a space velocity of about 0.05 to 0.6 hr$^{-1}$. Simultaneously, a gaseous ammonia charge is introduced into the reactor via a distribution device; e.g. a frit at the lower floor of the column, preferably in such an amount that the acrylonitrile and ammonia flow through the reaction chamber at a mole ratio of 2 : 1. According to the method of the present invention, the ammonia is completely absorbed as the gas bubbles rise. Furthermore, the ascending gas bubbles insure an intimate mixing of the reactants and thus an immediate reaction occurs resulting in the formation of bis-(2-cyanoethyl)-amine. The reaction product is removed at the lower end of the reactor above the distribution device. It is recovered as a clear liquid with a water content between 8 and 15% depending on the water concentration in the acrylonitrile. The yields obtained are greater than 90%.

The following example will explain in detail the process of the present invention.

EXAMPLE

The reaction takes place in a tube reactor which has an internal diameter of 36 mm and a length of 70 cm. At the lower end of the reactor there is a glass frit G 4, manufactured by the Schott Company, Mainz. It is designated 160 D and has a 30 mm diameter. The glass frit functions as a distribution device. The tube has a total volume of 700 ml. and the effective reaction volume (the space used during the reaction) equals 500 ml. 9 liters of gaseous ammonia are fed into the reactor per hour. The gas flows through the glass frit and reacts with the acrylonitrile. In order to monitor the gas conversion, the amount of unreacted gas is determined using a gas meter. 52 ml of acrylonitrile and 3.8 ml of water are pumped hourly into the upper end of the reactor at a rate which corresponds to a space velocity of 0.1 hr$^{-1}$. After 10 hours of residence time, the reaction mixture is removed at a point above the distribution device located at the lower end of the tube reactor. The yield of bis-(2-cyanoethyl)-amine obtained is 91 %.

This crude nitrile can then be hydrogenated in the usual manner.

What we claim is:

1. A process for the manufacture of bis-(2-cyanoethyl)-amine which comprises reacting gaseous ammonia with acrylonitrile having a 5–15% by weight water content in a bubble column reactor.

2. The process according to claim 1 wherein the reaction takes place at a temperature of about 20°–80° C.

3. The process according to claim 2 wherein the reaction takes place at a temperature of about 30°–60° C.

4. The process according to claim 1 wherein the gaseous ammonia and acrylonitrile are reacted in a mole ratio of 1 : 2.

5. The process according to claim 1 wherein the water containing acrylonitrile is added to the bubble column reactor at a space velocity of about 0.05 to 0.6 hr$^{-1}$.

* * * * *